United States Patent
Fleischer et al.

(10) Patent No.: US 7,851,202 B2
(45) Date of Patent: Dec. 14, 2010

(54) BIOSENSOR AND METHOD FOR OPERATING THE LATTER

(75) Inventors: Maximilian Fleischer, Höhenkirchen (DE); Corinna Haindl, Mannheim (DE); Hans Meixner, Haar (DE); Elfriede Simon, München (DE)

(73) Assignee: Siemens Aktiengesellschaft, Munich (DE)

( * ) Notice: Subject to any disclaimer, the term of this patent is extended or adjusted under 35 U.S.C. 154(b) by 573 days.

(21) Appl. No.: 10/588,493

(22) PCT Filed: Jan. 27, 2005

(86) PCT No.: PCT/EP2005/050343
§ 371 (c)(1), (2), (4) Date: Sep. 28, 2006

(87) PCT Pub. No.: WO2005/075994
PCT Pub. Date: Aug. 18, 2005

(65) Prior Publication Data
US 2008/0038749 A1    Feb. 14, 2008

(30) Foreign Application Priority Data
Feb. 5, 2004    (EP)    ............... 10 2004 005 710

(51) Int. Cl.
*C12M 1/34*    (2006.01)
*C12M 1/00*    (2006.01)
*C12Q 1/26*    (2006.01)
*C12Q 1/70*    (2006.01)

(52) U.S. Cl. ............... 435/287.2; 204/403.01; 435/5; 435/7.1; 435/25

(58) Field of Classification Search .......... None
See application file for complete search history.

(56) References Cited

U.S. PATENT DOCUMENTS 4,778,751 A * 10/1988 El Shami et al. ............. 435/7.5

(Continued)

FOREIGN PATENT DOCUMENTS

DE    43 18 519    12/1994

(Continued)

OTHER PUBLICATIONS

Niwa, O. et al. Electrochemical behaviour of reversible redox species at interdigitated array electrodes with different gwometries: consideration of redox cycling and collection efficiency. Anal. Chem. 1990; 62(5): 447-452.*

(Continued)

*Primary Examiner*—Mary E Mosher
*Assistant Examiner*—Stuart W Snyder
(74) *Attorney, Agent, or Firm*—Young & Thompson

(57) ABSTRACT

A biosensor for detecting an antigen using an antigen/antibody coupling includes: a silicon substrate, at least one interdigital electrode pair structure that is located on the silicon substrate, the electrode pair being interspaced at a maximum distance of 1.0 μm; a counter-electrode on the silicon substrate; a reference electrode; a first layer of protein, covering at least the interdigital electrode structure; a selective second protein layer applied to the first layer and containing a capture antibody selected specifically with respect to the antigen of interest and to which the antigen can be coupled. A sensor signal can be read on the interdigital electrode structure, if the antigen is coupled to the capture antibody by way of a sample to be analyzed that comes into contact with the biosensor and a redox reactive molecule is enzymatically released on the sensor surface by an enzyme-marked detection antibody likewise coupled to the antigen.

16 Claims, 3 Drawing Sheets

U.S. PATENT DOCUMENTS

| | | |
|---|---|---|
| 5,670,031 A | 9/1997 | Hintsche et al. |
| 5,945,294 A | 8/1999 | Frank et al. |
| 6,548,644 B1 * | 4/2003 | Pettit .................. 530/402 |
| 6,673,533 B1 * | 1/2004 | Wohlstadter et al. ......... 435/6 |
| 2002/0028441 A1 | 3/2002 | Hintsche et al. |
| 2005/0176067 A1 | 8/2005 | Fleischer et al. |

FOREIGN PATENT DOCUMENTS

| | | |
|---|---|---|
| DE | 196 10 115 | 9/1997 |
| GB | 2 276 724 | 10/1994 |
| WO | WO 00/11473 | 3/2000 |
| WO | WO 00/62048 | 10/2000 |

OTHER PUBLICATIONS

Niwa et al., "Electrochemical behavior of reversible redox species at interdigitated array electrodes with different geometries: consideration of redox cycling and collection efficiency", 1990, Anal Chem, vol. 62, pp. 447-452.*

"Electrochemical Behavior of Reversible Redox Species . . . "; Analytical Chemistry, American Chemical Society, Columbus, US, bd. 62. Nr. 5, 1990, pp. 447-452.

Sep. 9, 2007 European Search Report.

Niwa O et al: "Electrochemical Behavior of Reversible Redox Species at Interdigitated Array Electrodes With Different Geometries: Consideration of Redox Cycling and Collection Efficiency" Analytical Chemistry, American Chemical Society. Columbus, US, vol. 62, No. 5, 1990, pp. 447-452, XP000943524 ISSN: 0003-2700 p. 447-p. 448; table 1.

Kreuzer M P et al: "Development of an immunosensor for the determination of allergy antibody (IgE) in blood samples" Analytica Chimica ACTA, vol. 442, No. 1, Aug. 31, 2001, pp. 45-53, XP002347367 ISSN: 0003-2670 abstract.

Lu, Bin; Smyth, Malcolm R.; O'Kennedy, Richard: Immunological activities of IgG antibody on pre-coated Fc receptor surfaces. Analytica Chimica Acta, 1996, vol. 331, Nr. 1-2, S. 97-102. (abstract) CAPLUS [online]. In: STN. Accession No. 1996:596405.

Paeschke. M. [u. a.]: "Voltammetric Multichannel Measurements Using Silicon Fabricated Microelectrode Arrays". In: Electroanalysis, 1996, vol. 8, Nr. 10. S. 891-898.

Okochi M, Yokouchi H, Nakamura N, Matsunaga T.: Electrochemical detection of allergen in small-volume whole blood using an array microelectrode: a simple method for detection of allergic reaction. In: Biotechnology and Bioengineering, 1999, vol. 65, Nr. 4, S. 480-484.

Hintsche, R., M. Paeschke, et al. (1997). Microbiosensors using electrodes made in Si-technology. Frontiers in Biosensorics 1—Fundamental Aspects: 267-283.

Lyon, L. A., M. D. Musick, et al. (1999). "Surface plasmon resonance of colloidal Au-modified gold films." Sensors and Actuators B 54: 118-124.

Uttenthaler, E., C. Köβlinger, et al. (1998). Quartz crystal biosensor for the detection of the African Swine Fever diseas.

Schindler, F. (1992). "Real-Time BIA." BioTec 1: 36-43.

* cited by examiner

Electrode processes:

BIOSENSOR AND METHOD FOR OPERATING THE LATTER

The invention relates to a biosensor which is equipped with a coating for verifying antigen/antibody reactions.

In modern analytics and above all in modern clinical diagnostics the demand for simple and rapid test methods which are very cost effective as well is growing all the time. In particular systems which can determine a large number of analyses within a short time, such as high throughput screening methods for example, e.g. in medicine production, environmental or foodstuffs analysis or can almost simultaneously investigate and distinguish between many different analytes (e.g. by means of sensor arrays), e.g. for differentiation of analytes for differential diagnostics, are required in such cases. Interest is focused primarily on test systems which are small and portable and are suitable for one-time use.

Antigen/antibody reactions stand out quite especially by virtue of a very high selectivity and also sensitivity. The specificity of these antigen/antibody reactions can be used in the development of new technologies, known as immunosensors. In this case the molecular binding occurrence between an antibody and a substance to be verified (antigen) is converted into a macroscopically measurable sensor signal. All molecules capable of binding which couple with an antibody can be used as substances to be verified. Antigen is generally taken to mean an alien substance which evokes in the body the formation of antibodies against itself.

An allergen is a substance triggering an allergy, such as pollen, hair, dust etc. for example, which can give rise to an allergy in humans who are especially sensitive to such substances. The allergy is thus a pathological reaction of the body to specific substances alien to the body.

An antibody is a protective substance (protein) detectable in the blood serum which is formed as a reaction to the intrusion of antigens.

The antigen-antibody reaction means connecting an antigen to the specific antibody directed against this antigen to form an antigen-antibody complex (immunocomplex).

Various methods of detecting the antigen/antibody exist for verification of different antigens. The different readout methods are explained in brief below.

Piezoelectric immunosensors based on mass-sensitive crystal oscillators which act as transducers. The change of the mass-dependent resonant frequency of the quartz crystal gives information about the number of bound analytes on the quartz [VI]. Potentiometric immunosensors evaluate the shift in potential arising from the antigen/antibody reaction on an electrode surface [III].

Optical Immunosensors [V; IV]

a. Direct measurement methods: e.g. ellipsometry or surface plasmon resonance are used to derive conclusions about the volume of bound analyte from the layer depth increase by formation of the affinity complex.

b: Indirect measurement methods: In this case a marking, i.e. a chemical modification of one of the immunocomponents is needed for detection of a measurable signal.

b.1. Radioimmunoassay If this marker is a radioactive isotope, the concentration of bound marked substance is determined by measurement of the isotope decay. More frequently however an optical signal is created.

b.2. Fluorescence immunoassay for example an immunocomponent carries a fluorescence marker, the intensity of the fluorescence leads to the sensor signal.

b.3. Enzyme immunoassays are based on the existence of an enzyme-marked reaction partner.

After a suitable substrate is added, the enzymes catalyze a splitting reaction to an optically active molecule. The sensor signal is then read out either photometrically, i.e. a color reaction is detected, or through chemiluminescence.

The object of the invention is to provide a biosensor for verifying a selected antigen/antibody reaction and a method of operation, with a plurality of analytes able to be detected with high sensitivity.

This object is achieved in each case by the corresponding combination of features of claim 1 or 8. Advantageous embodiments can be taken from the subclaims.

The invention is based on the general knowledge that

Antigen/antibody reactions can be marked with an enzyme-coupled detection antibody, Specific proteins such as for example protein A, G, or G' cause a directed binding of the antibody molecules, A redox recycling through enzymatic splitting of for example pAP (para aminophenol) at IDS can be induced, For electrochemical readout of the redox recycling a counter-electrode and a reference electrode are necessary,

BRIEF DESCRIPTION OF THE DRAWINGS

Exemplary examples are described below with reference to schematic drawings which do not restrict the invention.

Figure 1:
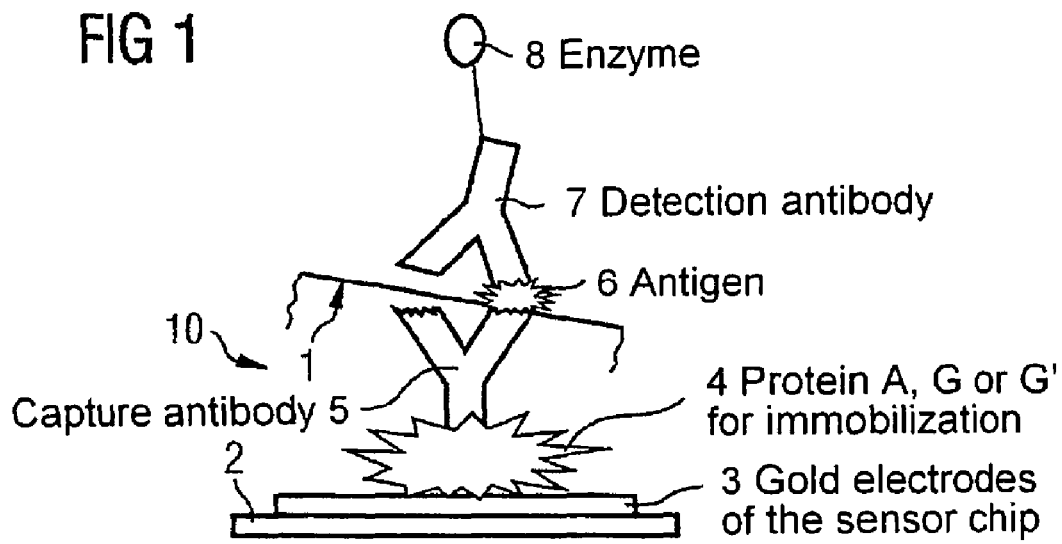
FIG. 1 shows a schematic layout of a test system based on an antigen/antibody reaction at the gold electrodes of a sensor chip, or biochip.

Layout of a biosensor able to be read out electronically with corresponding characteristics for verifying an antigen-antibody reaction:

The silicon chips which are contacted via a circuit board with the readout device carry a different number of interdigital electrode structures 12 depending on layout, which are arranged in pairs, that is always node/cathode, and depending on chip layout have a variable diameter, (with the same diameter always being used on one chip). The electrodes (13) are comb-like electrode fingers of the interdigital structures always have a width of 1 μm in such cases and a spacing between the electrode pairs of a maximum of 1.0 μm, in addition there is a electrode made of gold on the chip. The Ag/AgCl reference electrode 9, against which the electrode potential is set, is not located on the chip, it is integrated into the flow system and can however optionally also be realized on the chip.

The antibody 5 is immobilized on the gold electrodes of the sensor chip, or biochip. This occurs, depending on the type of the antibody 5, with the aid of a protein layer made of protein A, G or G'.

The antigen 6 to be verified, the analyte, will bind by means of antigen/anti body coupling to the antibody 5 immobilized on the biochip.

This binding is verified by means of an enzyme-marked second antibody 7.

The sensor signal is read out electrically with a multichannel potentiostat, with which a constant potential is applied to the interdigital electrode pair, after enzymatic release of a redox-reactive molecule (such as for example p-aminophenol) on the sensor surface 1.

Figure 4:
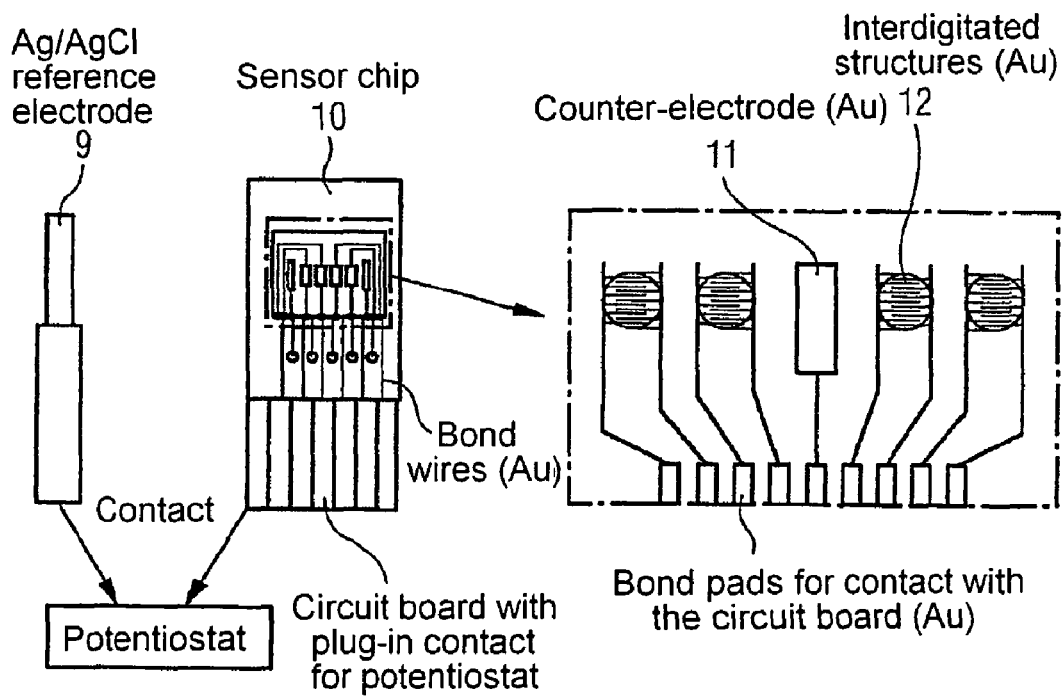
FIG. 4 shows the schematic diagram of the sensor chip used with reference electrodes, plug-in contact for micropotentiostats and an enlarged view of the silicon chip with interdigital structures and counter-electrode.

The biosensor is based on a silicon chip with gold interdigital structures, FIG. 4, in the micrometer range, with the electrode pair spacing being less than 1 µm. Lit [I] and [II].

The antigen verification is to be realized by the following layer structure on the gold Interdigital structures of the sensor chip, or biochip, FIG. 1.

Chip Coating:

First step is fabricating a protein-based coating, which is produced by adsorption of e.g. protein A, G, G' or L directly on the gold surface of the interdigital structure, where the selection of the protein depends on the type of the capture antibody 5.

Second step is the directed binding of the capture antibody 5 to the first protein base layer. This creates a defined and highly-selective chip surface.

Measurement for Detection of the Antigen or of the Analyte:

After the contacting of the chip surface 1 with the sample to be analyzed, for example water sample, serum, food extract etc., which contains the corresponding analyte/antigen, the antigen is selectively bound to the capture antibody 5. The antigens include all molecules which can be bound by or to an antibody; these can be high-molecular organic compounds, such as antibodies, but also proteins, protein fragments, microorganisms, tumor markers, toxins or low-molecular organic compounds such as medicines, pesticides, antibiotics, antimycotics of aromatic hydrocarbons.

The bound antigen 6 is marked by a detection antibody 7.

The schematic layout of the system for operation of a biosensor based on an antigen/antibody reaction, which can be read out accordingly at the gold electrodes 3 of the sensor chip 10, or biochip of FIG. 1.

Figure 2:
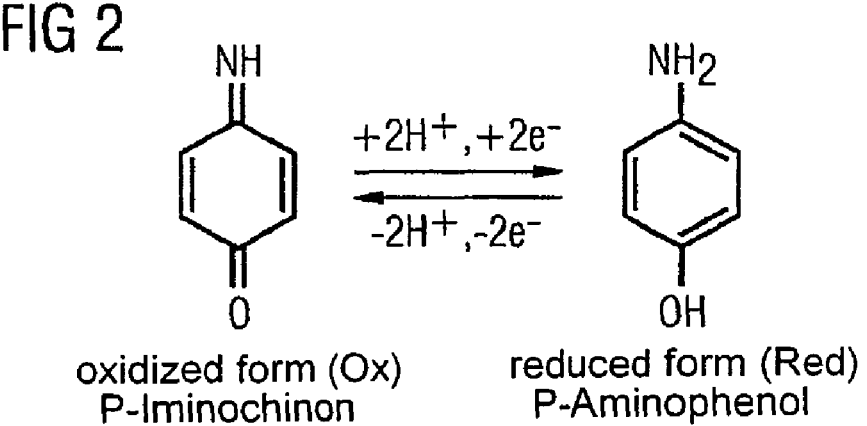
FIG. 2 shows electrode processes at the interdigital electrodes for the amperometric readout reaction with p-aminophenol.
Figure 2:
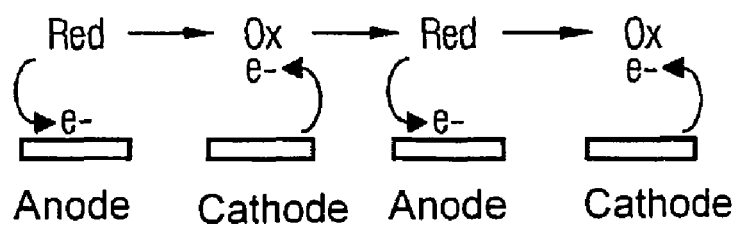

For electrical readout the biochip is contacted with a potentiostat FIG. 2 and the substrate suitable for the enzyme to be used, e.g. p-aminophenyl phosphate is fed via a fluid system FIG. 2. Through the enzyme alcalic phosphatase, coupled to the detection antibody 7 the substrate para aminophenyl phosphate is converted into the redox-active p-aminophenol. For a specific voltage, for example 350 mV, applied between the electrodes of the biochip the released p-aminophenol undergoes a reduction and subsequent oxidation at the cathodes and anodes of the interdigital electrodes 12 FIG. 2, generating a change in the sensor signal as a measurable current in the nA range.

As well as the amperometric readout under constant voltage method described, a detection using alternating current or by means of cyclic voltammetry can also be considered however.

Electrode processes at the interdigital electrodes for the amperometric readout reaction with p-aminophenol are shown in FIG. 2.

Another enzyme-bound detection antibody 7 can also be used for detection. Another suitable substrate rather than p-aminophenyl phosphate must then however also be used which reacts to the enzyme used. Further suitable enzyme-bound antibodies or their substrates are: (β-Galactosidase, coupled to the detection antibodies and p-aminophenyl-β-D Galactopyranoside as substrate.

The major advantages of the invention lie in the fact that, with the aid of this for example amperometric antibody biochip, a plurality of antigens can be verified through corresponding selection of the antibody.

The system stands out compared to conventional methods by
- its small size,
- the short duration of the test (<10 min) and
- its high sensitivity.

Because of these characteristics and the low fabrication costs of the silicon chip the measurement system is suitable as a "one-time analysis system" for
- Medical diagnostics
- Foodstuff monitoring
- Environmental monitoring
- Checking drinking water
- Safety systems (detection of bio weapons such as anthrax, smallpox)
- Drug/doping tests
- No sample preparation is normally needed.

By using an electrical biochip, the disadvantages of optical methods, which above all lie in the major apparatus overhead, can be reduced.

Measurement Layout:

a) Measuring Position

Figure 3:
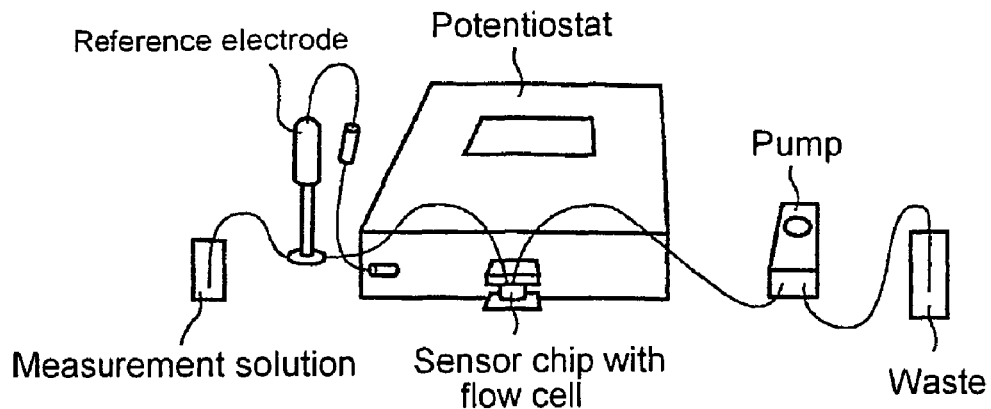
FIG. 3 shows a schematic layout of a measuring position for reading out the sensor chip signal.

A schematic layout of the measuring position for reading out the sensor chip is shown in FIG. 3.

b) Layout of the Sensor Chip System

A schematic diagram of the sensor chip used with reference electrode 9, plug-in contact for micropotentiostat and enlarged view of the silicon chip with interdigitated structures 12 and counter-electrode 11 is shown in FIG. 4.

As an alternative to the external reference electrode the Ag/AgCl electrode can also be located on the silicon chip.

c) Interdigital Electrode Structures

Figure 5:
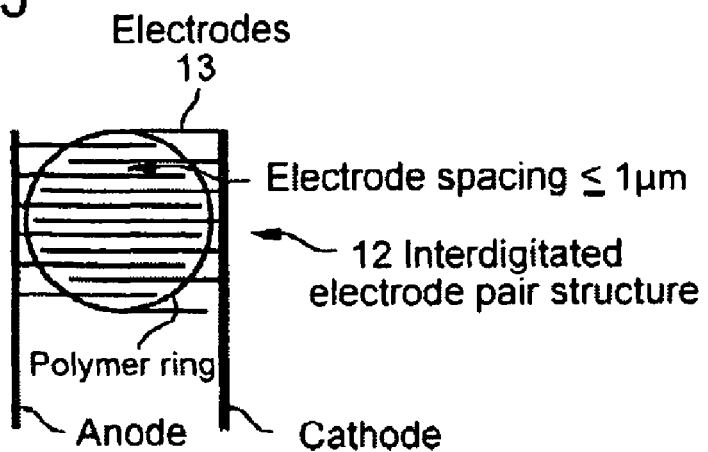
FIG. 5 shows a schematic layout of an interdigital structure.

A schematic layout of an interdigital electrode structure is shown in FIG. 5.

Using a mouse immunglobulin G (IgG) as an example of an antibody and anti-mouse IgG coupled to alcalic phosphatase as antigen 6, the operability of the measurement principle presented has been tested. In this case two positions, corresponding to two interdigital electrode pair structures 12, of a chip are coated and read out in parallel. By means of protein A mouse IgG has been bound to the electrode surface as capture antibody 5. Since anti-mouse IgG is already enzyme-bound, the antigen/antibody reaction in this case also simultaneously represents the detection step. Subsequently the chip is read out. For this the sensor is built into the flow cell, contacted with the multichannel potentiostat and initially flushed with buffer. After the addition of p-aminophenyl phosphate there is a wait of about 30 seconds and then the flow is stopped, FIG. 6.

Figure 6:
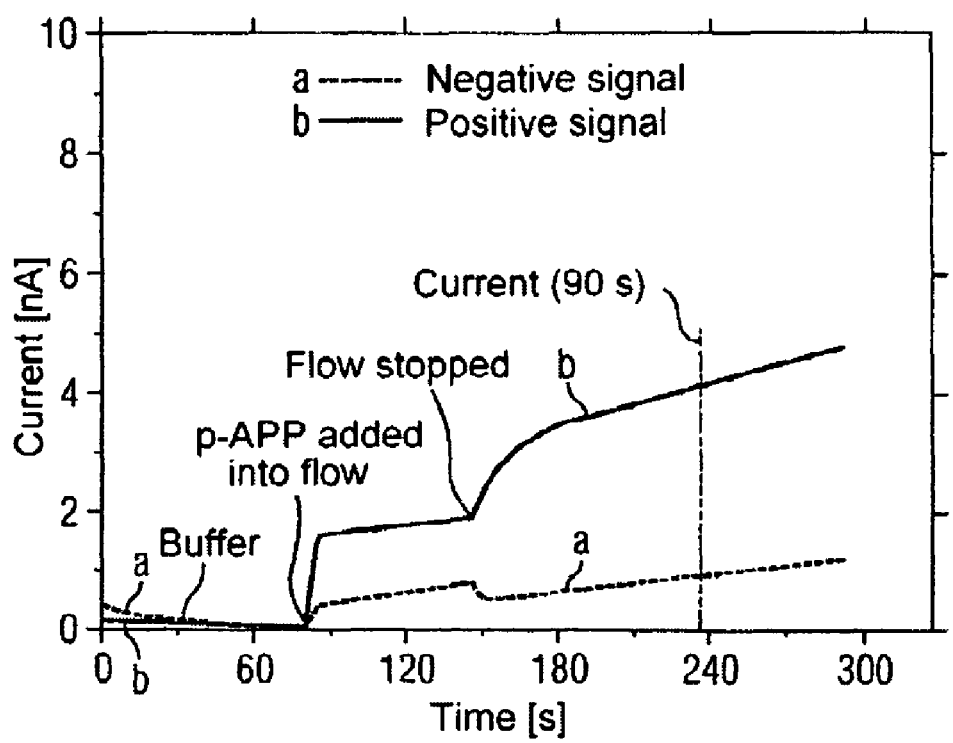
FIG. 6 shows an example of a sensor signal with positive (protein A, mouse IgG, anti-mouse IgG (AP)) and negative sample (protein A, mouse IgG).

FIG. 6 shows an example of a sensor signal with positive, that is available analyte, (protein A, mouse IgG, anti-mouse IgG (AP)) and negative sample (protein A, mouse IgG).

It can be seen from FIG. 6 that, on addition of the substrate p-aminophenyl phosphate (p-APP) at both positions, an increase in the sensor signal occurs although p-aminophenol will only split off at the positive position. The reason for this is that with the flow switched on, p-aminophenol generated at the positive position is subject to active transport within the cell For this reason the behavior of the relevant positions when the flow stops is observed for evaluation of the sensor signal. In the case of a positive signal response, the signal increases at flow stop. The reason for this lies in the increasing concentration of p-aminophenol at the enzyme-occupied position, which is not transported away by the flow. Simultaneously the p-aminophenol arising is not transported to the neighboring negative position, so that the concentration and thus also the measurable current signal there collapses when the flow is switched off.

LITERATURE

[I] Hintsche, R. and M. Paeschke (2000). Detektion von Molekülen und Molekütlkomplexen (detection of molecules and molecule complexes). Patent DE 19610115C2. Germany.
[II] Hintsche, R., M. Paeschke, et al. (1997). Microbiosensors using electrodes made in Si-technology. Frontiers in Biosensorics 1—Fundamental Aspects: 267-283.
[III] Paeschke, M., F. Dietrich, et al. (1996). "Voltammetric Multi channel Measurements Using silicon Fabricated Microelectrode Arrays." Electroanalysis 8(10):891-898.
[IV] Lyon, L. A., M. D. Musick, et al. (1999). "Surface plasmon resonance of colloidal Au-modified gold films." Sensors and Actuators B 54:118-124.
[V] Schindler, F. (1992). "Real-Time BIA." BioTec 1: 36-43.
[VI] Uttenthaler, E., C. Köβlinger, et al. (1998). Quartz crystal biosensor for the detection of the African Swine Fever disease.

The invention claimed is:

1. A biosensor for detection of an antigen (6) by means of an antigen/antibody coupling, consisting of the following elements:
    a silicon substrate (2),
    at least one interdigital electrode pair structure (12) of electrodes (13) arranged in pairs accommodated on the silicon substrate (2) with a spacing between the electrode pairs of maximum 1.0 µm,
    counter-electrode (11) accommodated on the silicon substrate (2),
    a reference electrode integrated onto the silicon substrate (2),
    a first layer made of protein (4) at least covering over the interdigital electrode structure (12),
    a selective second protein layer applied over the first layer which contains a selected capture antibody (5) corresponding to the detecting antigen (6) and which can couple to the antigen, and
    the capture antibody (5) is immobilized over the interdigital electrode structure (12) by the protein (4) of the first layer;
    wherein if an antigen (6) is bound to the capture antibody (5) and the enzyme-labeled detection antibody is (7) also bound to the antigen, an enzymatic release of a redox-reactive molecule on the sensor surface (1) occurs and a sensor signal being able to be read out at the interdigital electrode structure (12) is generated.

2. The biosensor as claimed in claim 1, in which the first protein layer consists of the Protein A, Protein G or Protein G'.
3. The biosensor as claimed in claim 1, in which a signal is detected using alternating current or cyclic voltammetry.
4. The biosensor as claimed in claim 1, which is coupled with a potentiostat for readout of the sensor signal.
5. The biosensor as claimed in claim 1, in which the sample to be analyzed is provided as fluid on the surface (1) of the biosensor via a flow system.
6. The biosensor as claimed in claim 1, in which interdigital electrode structures (12) and counter-electrode (11) are made of gold.
7. The biosensor as claimed in claim 1, in which the reference electrode represents an Ag/AgCl reference electrode.
8. The biosensor as claimed in claim 1, in which the antigen (6) is simultaneously an allergen.
9. The biosensor as claimed in claim 1, in which the antigen (6) is a protein, a polypeptide or oligopeptide.
10. The biosensor as claimed in claim 1, in which the antigen is a bacterium or a virus.
11. The biosensor as claimed in claim 1, in which the antigen is an organic compound selected from the group consisting of a toxin, a medicine, a pesticide, anthrax, an antibiotic and an aromatic hydrocarbon.
12. A method for operation of the biosensor of claim 1 for detection of an antigen (6) by means of antigen/antibody coupling, comprising the following steps:
    coating a biosensor constructed on a silicon chip with a protein base coating with a protein A, G or G' with simultaneous covering of interdigital electrode pair structures (12) on the surface of the silicon chip;
    fabricating a further layer on the protein coating which contains a capture antibody (5) which is selected so that it can coupled with the antigen (6) sought;
    contacting the sensor surface (1) with a fluid to be analyzed;
    contacting the sensor surface (1) with an enzyme-labeled detection antibody (7);
    contacting the sensor surface (1) with redox-reactive molecule specific to the enzyme that labels the detection antibody (7); and
    monitoring a presence of a reaction product of the redox-reactive molecule on the sensor surface (1);
    wherein detection of the presence of the reaction product indicates the presence of the antigen.
13. The method as claimed in claim 12, in which the capture antibody (5) features a directed binding to the protein (4) of the first layer.
14. The biosensor as claimed in claim 2, in which a signal is detected using alternating current or cyclic voltammetry.
15. The biosensor as claimed in claim 2, which is coupled with a potentiostat for readout of the sensor signal.
16. The biosensor as claimed in claim 2, in which the sample to be analyzed is provided as fluid on the surface (1) of the biosensor via a flow system.

* * * * *